United States Patent

Hoyns

Patent Number: 5,759,154
Date of Patent: Jun. 2, 1998

[54] PRINT MASK TECHNIQUE FOR ECHOGENIC ENHANCEMENT OF A MEDICAL DEVICE

[75] Inventor: Dirk V. Hoyns, Conyers, Ga.

[73] Assignee: C. R. Bard, Inc., Murray Hill, N.J.

[21] Appl. No.: 772,972

[22] Filed: Dec. 23, 1996

[51] Int. Cl.$^6$ ............................................. A61B 8/00
[52] U.S. Cl. ................................ 600/458; 29/DIG. 16
[58] Field of Search ............................ 128/662.02, 662.05; 29/DIG. 16; 600/458, 461, 464

[56] References Cited

U.S. PATENT DOCUMENTS

| | | |
|---|---|---|
| 4,401,124 | 8/1983 | Guess et al. |
| 4,431,006 | 2/1984 | Trimmer et al. |
| 4,642,168 | 2/1987 | Imai . |
| 4,711,706 | 12/1987 | Wasel et al. |
| 4,869,259 | 9/1989 | Elkins . |
| 4,977,897 | 12/1990 | Hurwitz ............... 128/662.05 |
| 5,383,466 | 1/1995 | Partika . |
| 5,490,521 | 2/1996 | Davis et al. .......... 128/662.02 |
| 5,611,345 | 3/1997 | Hibbeln ............... 128/662.05 |

Primary Examiner—Francis Jaworski
Attorney, Agent, or Firm—Jones & Askew, LLP

[57] ABSTRACT

An echogenically enhanced medical device and method for manufacture are disclosed. A mask is applied to the surface of the medical device, and portions of bare metal are exposed through the mask. The masked device is subjected to a process which removes material from the exposed portions. The resulting depressions enhance echogenicity of the device under ultrasound. In a preferred embodiment the depressions comprise alternating rows of squares and diamonds disposed around the circumference of the device.

14 Claims, 4 Drawing Sheets

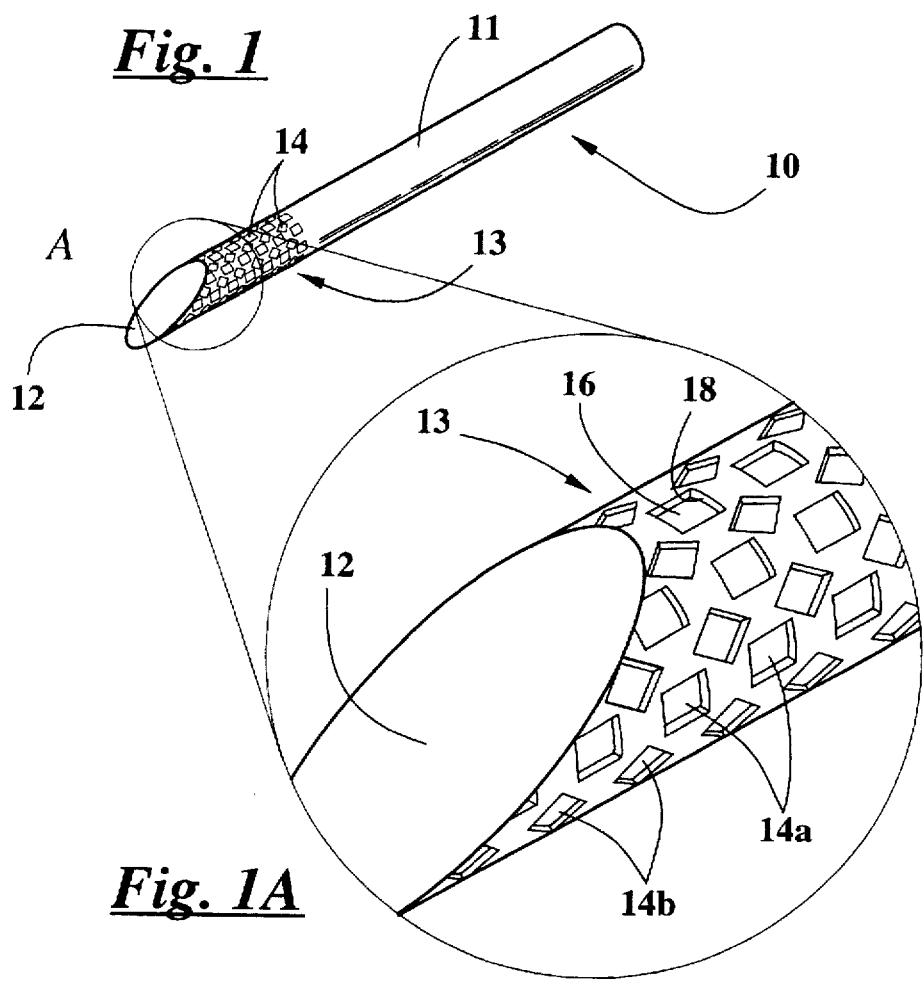
*Fig. 1*
*Fig. 1A*
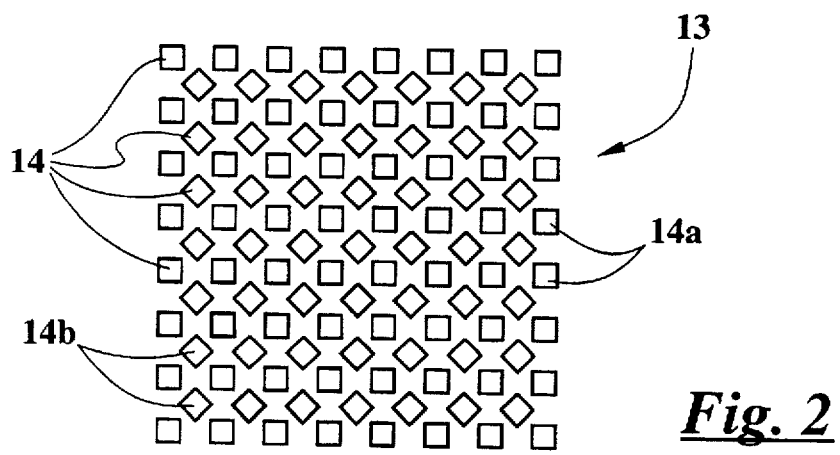
*Fig. 2*

5,759,154

PRINT MASK TECHNIQUE FOR ECHOGENIC ENHANCEMENT OF A MEDICAL DEVICE

TECHNICAL FIELD

The present invention relates generally to medical devices and relates more specifically to a medical device and method of manufacture which is echogenically enchanced to improve its visibility under ultrasound.

BACKGROUND OF THE INVENTION

Ultrasound technology has widespread medical applications for visualizing internal tissues and organs. Because of its ability to display tissues and organs in real time, ultrasound is widely used as a means for guiding minimally invasive medical instruments, such as diagnostic sampling devices. Core biopsy needles, aspiration biopsy needles, and amniocenteses needles are examples of medical devices which are advantageously guided under ultrasound visualization.

Ultrasound works by a transducer sending out pulses of ultra high-frequency sound waves, typically in the frequency range of 4.5–12 mHz. Echos off of the target tissues are received by a transducer array. The return signal is then processed, and an image corresponding to the target tissues is displayed on a monitor. Different tissue types have different densities and elastic properties, which affect the propagation velocity of the sound wave traveling through them. Since the velocity of a sound wave changes at the interface of two mediums with different densities, a portion of the sound waves is reflected by the interface. These properties allow the ultrasound system, and the sonographer, to differentiate the various internal organs and tissue types.

Ultrasound reflections can be either specular (mirror-like) or scattered (diffuse). Biological tissue typically reflects ultrasound in a scattered manner, with a percentage of the reflected wave being returned to the transducer array. The amount of reflection of the biological tissue which return to the transducer array enables the differentiation that is visible on the ultrasound display. In comparison to biological tissue, a needle has a very high density and characteristic impedance, making it a very effective reflector. Because of its smooth surface finish, a conventional needle reflects ultrasound waves in a specular manner.

Because the needle's surface reflects ultrasound in a specular manner, the needle is difficult to visualize under ultrasound at incident beam angles of less than or equal to 60° from the needle surface. Basic laws of specular reflection state that the angle of incidence is equal to the angle of reflection. For example, if the angle of incidence is 30° from the needle surface, the angle of reflection is also equal to 30° from the needle surface in the opposite quadrant. Thus the ultrasound beam is traveling at the angle an of 120° away from the incident beam, completely missing the transducer array. As the angle of incidence approaches perpendicular, that is, greater than 60° from the needle surface, the likelihood is better that some of the reflective ultrasound beam will be collected by the transducer array.

Efforts have been made to enhance the echogenicity of surgical needles by treating the surface of the needle. In U.S. Pat. No. 4,401,124, a needle is disclosed which has a diffraction grating inscribed on the surface of the needle. When the ultrasound waves strike the diffraction grating, the waves that strike the spaces between the grooves are reflected specularly at an angle equal to the incident angle, as they would at a plain needle. However, the waves that strike the grooves are diffracted into "wavelettes," or secondary wave fronts. The secondary waves then leave the diffraction grating traveling in many different directions, that is, scattered. Only a percentage of the reflective wave is scattered in direction which is returned to the transducer array.

Other approaches to enhancing the echogenicity of needles by scattering the incident ultrasound wave are disclosed in U.S. Pat. No. 4,869,259 and U.S. Pat. No. 5,801,997. A surgical needle disclosed in U.S. Pat. No. 4,869,259 has a portion of its surface particle-blasted to produce a uniformly roughened surface. The particle-blasted surface scatters the incident ultrasound beam such that a portion of the scattered beam is picked up by the ultrasound array. U.S. Pat. No. 5,081,997 the opposite approach is used, in that the surface of the needle is treated to provide sound reflective particles imbedded in the surface of the needle. The mechanism by which the particles work is similar to that of the particle-blasted surface of U.S. Pat. 4,869,259, in that the particles scatter the incident ultrasound beam such that a portion of the scattered beam is reflected back to the ultrasound array.

U.S. Pat. No. 5,383,466 discloses a needle which is coated at selected locations along its links with deposits of a material having a matrix of gas bubbles contained in a polymeric material. The gas bubbles exhibits high reflectivity of ultrasound energy and provides for good differentiation between the material and surrounding tissues.

U.S. Pat. No. 4,977,897 discloses a needle which employs a different means for enhancing ehcogenisity. The needle has one or more cross-drilled holes formed in the needle and running perpendicular to the axis of the needle. The cross-drilled hole provides an air gap which is an area of significantly different density and characteristic impedance from that of the needle. Since air is hyperechoic under ultrasound, it provides for differentiation from the surrounding tissues. In addition, the edge of the hole also acts as a diffuser, scattering the ultrasound beam such that a portion of the scattered beam is picked up by ultrasound transducer.

A drawback to most, if not all, of the prior art approaches to enhancing echogenicity of a medical instrument is that the means for enhancing echogenicity is based upon a scattering or diffusion of the incident ultrasound wave. Because the incident ultrasound beam is scattered in all directions, only a percentage of the beam is reflected in a direction which can be picked up by the ultrasound array. Thus the return signal is relatively weak. Thus it would be desirable to provide a means for enhancing echogenicity of a needle which would provide a stronger return signal, and hence render the instrument more visible under ultrasound than the means disclosed in the aforementioned prior art patents. It would also be desirable to provide a means for enhancing the echogenicity of a medical instrument which provides a more specular reflection, such that a greater portion of the incident ultrasound beam is reflected back toward the ultrasound array.

SUMMARY OF THE INVENTION

Stated generally, the present invention comprises an echogenically enhanced medical device which provides a stronger return signal, and hence renders the instrument more visible under ultrasound. The echogenically enhanced medical device of the present invention provides a more specular reflection at shallow angles of incidence, such that a greater portion of the incident ultrasound beam is reflected back toward the ultrasound array. The present invention further comprises a method for manufacturing an echogenically enhanced medical device which comprises imprinting a mask on the needle and then subjecting the masked needle to a process which removes metal from the unmasked portions of the needle surface.

Stated somewhat more specifically, the present invention relates to an echogenically enhanced medical device. The body of the device is comprised of an echogenically reflective material. A plurality of depressions having substantially straight sides and substantially flat bottom and side walls are formed in the surface of the device, said depressions. In a disclosed embodiment, the device has rows and bands of square depressions having two sides substantially parallel to an axis, interspaced by alternate rows and bands of square depressions having two sides oriented substantially diagonally with respect to said axis.

In another aspect the invention relates to a method for manufacturing an echogenically enhanced medical device. A mask is imprinted on the surface of an object, leaving portions of the surface of the object exposed through the mask. The masked object is then subjected to a process which removes material from the portions of the surface of the object which are exposed through the mask. In the disclosed embodiment the mask is comprised of a non-conductive material, and the object is electro-polished to remove portions of the surface of the object exposed through the mask.

Thus it is an object of the present invention to provide a medical device which is more easily seen under ultrasound imaging.

It is another object of the present invention to provide a medical device which provides a stronger return signal of an incident ultrasound beam to the ultrasound array.

Still another object of the present invention is to provide a medical device which provides a more specular reflection of an ultrasound beam at shallow angles of incidence.

Another object of the present invention is to provide a method of manufacturing an improved medical instrument having these desired characteristics.

Other objects, features, and advantages of the present invention will become apparent upon reading the following specification, when taken in conjunction with the drawings and the appended claims.

BRIEF DESCRIPTION OF THE DRAWINGS

FIG. 1 is a perspective view of an echogenically enhanced needle according to the present invention; FIG. 1A is an enlarged view of the portion of FIG.1 indicated by the circle A.

FIG. 2 is a depiction of a preferred pattern of depressions for forming a matrix in the surface of a needle to reflect ultrasound waves in a substantially specular manner.

DETAILED DESCRIPTION OF THE DISCLOSED EMBODIMENT

Figure 3A:
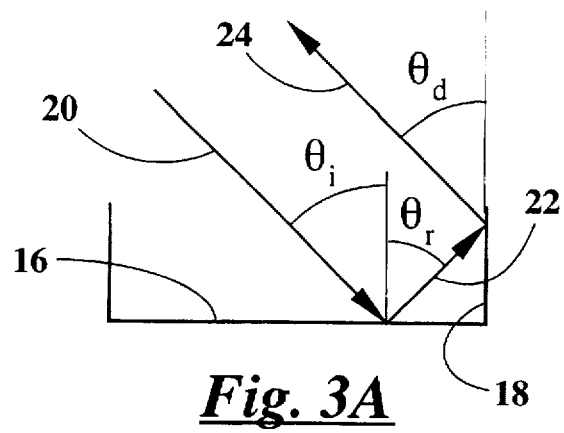
FIGS. 3A and 3B are diagrams which illustrate the reflection of an ultrasound beam by an individual depression of the matrix of depressions of the surface of the needle of FIG. 1 for different angles of incidence of tile ultrasound beam.

Referring now to the drawings, in which like numerals indicate like elements throughout the several views, FIG. 1 illustrates an echogenically enhanced needle 10 according to the present invention. The needle 10 of the disclosed embodiment is a stylette of a coaxial core biopsy needle assembly, commonly known as a "Tru-Cut"-type needle. The needle 10 is a solid rod of surgical-grade stainless steel and includes a shaft 11. The forward end of the shaft 11 is formed into a sharpened cutting surface 12. The portions of the needle 10 thus far described, including the shaft 11 and sharpened cutting surface 12, are of conventional design and are well-known to those skilled in the art.

The forward end of the shaft has a matrix 13 of depressions 14 formed around its circumference. The matrix 13 is shown in more detail in FIG. 2 and consists of staggered rows and columns of substantially square depressions 14. Alternate rows and columns are comprised of substantially square depressions 14a whose sides are aligned either parallel or perpendicular to the longitudinal axis of the shaft 11 of the needle 10, while the remaining rows and columns are comprised of depressions 14b having sides which are oriented diagonally with respect to the longitudinal axis of the shaft 11 of the needle 10. For convenience of description, the depressions 14a whose sides are aligned either parallel or perpendicular to the longitudinal axis of the shaft 11 of the needle 10 may be referred to hereinbelow as "squares," while the depressions 14b whose sides are oriented diagonally with respect to the longitudinal axis of the shaft 11 of the needle 10 may be referred to as "diamonds." However, it will be understood that the squares 14a and diamonds 14b are actually of identical configuration and differ only in the manner in which they are aligned.

Figure 3B:
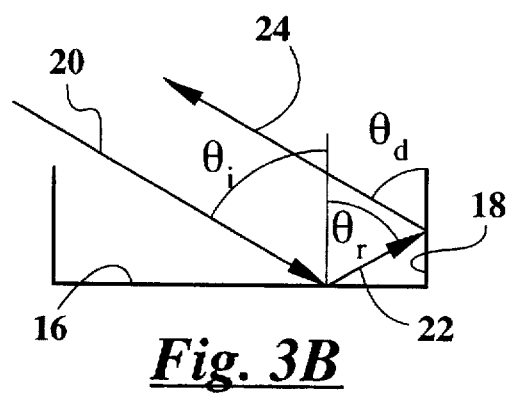

Referring now to FIGS. 3A and 3B, each depression 14 includes a bottom wall 16 and side walls 18. The bottom and sides walls 16, 18 of each depression 14 are arranged to reflect an incident ultrasound beam back along the same line as the incident beam. In the following discussions, ultrasound beams will be represented as vectors for the sake of simplicity. In fact, ultrasound is a longitudinal wave and may be considered as an infinite number of vectors perpendicular to the wave front.

FIG. 3A illustrates the reflection of an incident ultrasound beam 20 striking the needle 10 at an angle of incidence $\theta_i$ of about 45°. The incident beam 20 strikes the base 16 of the depression 14 and reflects upward at an angle of reflection $\theta_r$ equal to the angle of incidence $\theta_i$ of the incident beam 20, that is, 45°. The reflected beam 22 strikes the side wall 18 of the depression 14 and reflects a second time at an angle of departure $\theta_d$ equal to the angle of the reflected beam $\theta_r$, which is equal to the angle of incidence $\theta_i$. Thus the return beam 24 is reflected by the depression 14 to return along the same line of travel as the incident ultrasound beam 20.

FIG. 3B illustrates the reflection of an incident ultrasound beam 20 which strikes the needle 10 at a shallower angle. In FIG. 3b, the angle of incidence $\theta_i$ is equal to 60°. The incident beam 20 strikes the bottom wall 16 of the depression 14 and reflects upward at an angle of reflection $\theta_r$ of 60°. The reflected beam 22 then strikes the side wall 18 of the depression and reflects at a departure angle $\theta_d$ of 60°. Thus the return beam 24 is again reflected back along the line of travel of the incident beam 20.

While not illustrated in FIGS. 3A and 3B, it will be appreciated that incident ultrasound waves which strike the side wall 18 of the depression 14 first will reflect downward and then reflect off the bottom wall 16 of the depression to return along the same line as the incident beam.

With further reference to FIGS. 3A and 3B, it will be appreciated that there are certain trade-offs inherent in selecting the depth of the depression 14. A shallower depression enables an incident beam arriving at a shallower angle to reflect off the bottom wall 16 of depression 14 and hence off the side wall 18. However, for a steeper angle of incidence, a shallower depression results in a side wall 18 of a lower height, such that a greater percentage of the incident beam will reflect over the top of the side wall 18, missing the side wall altogether. Conversely, a deeper depression 14 will result in a side wall 18 having a greater height, such that an incident beam striking the needle 10 at a relatively steep angle and reflecting off the bottom wall 16 will be more likely to strike the higher side wall 18 and return to the ultrasound array. However, for a deeper depression 14, ultrasound waves which strike the needle 10 at a shallow angle will never strike the bottom wall 16 directly. Further, any portion of the beam which strikes the side wall 18 directly will reflect downward and bounce off the bottom wall 16; but rather than returning to the ultrasound transducer, the reflected wave will strike the opposite side wall 16 and reflect away from the transducer array. Thus, the depth of the depressions 14 must be selected so as to strike a suitable balance between these limitations. A suitable configuration for the depressions 14 has been determined to be a depth equal to about 30% of the width of the depression.

Figure 4:
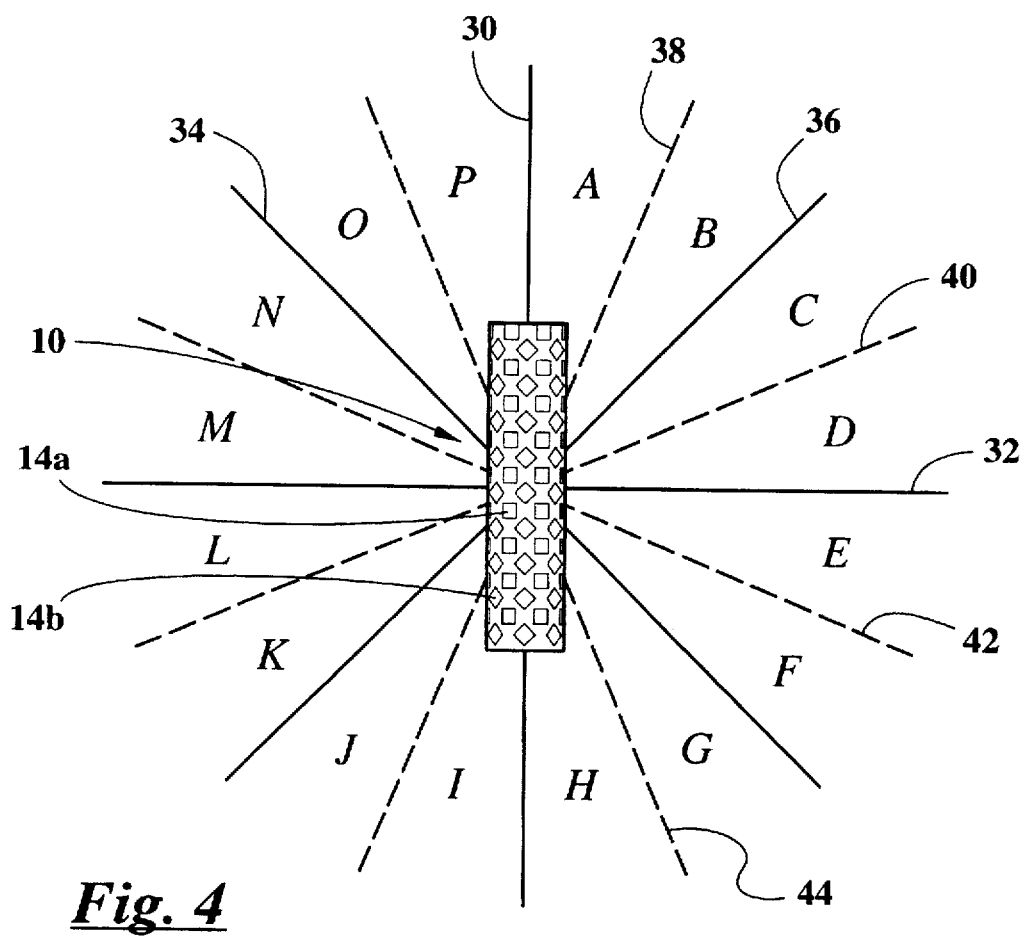
FIG. 4 is a diagram of the needle of FIG. 1 showing the longitudinal and lateral axes of the needle and showing lines representing diagonals with respect to the longitudinal and lateral axes.

FIG. 4 illustrates a needle 10 having a longitudinal axis 30 and a transverse axis 32. Diagonal lines 34 and 36 bisect the quadrants formed by the longitudinal and transversed axes 30, 32. Dashed lines 38, 40, 42, and 44 bisect each of the angles formed by the longitudinal axis 30 and the diagonal lines 34, 36, and the transverse axis 32 and the diagonal lines 34, 36. The plane of the needle as illustrated in FIG. 4 is thus divided into sixteen sections, indicated by the letters A through P. From an examination of this figure, it will be appreciated that, regardless of the angle of the needle 10 with respect to an ultrasound transducer, an ultrasound beam will always be within 22.5° of striking a side wall 18 of a depression 14 perpendicularly. As an example, an incident ultrasound beam arriving at the needle 10 from a location in section A will strike a side wall of a depression 14a parallel to the transverse axis 32 at an angle of less than 22.5°. Similarly, an incident ultrasound beam arriving from a location in section B will strike a side wall of a diamond-shaped depression 14b at an angle of incidence less than or equal to 22.5°. Since a satisfactory return signal can be received by the transducer array if the angle of incidence is less than about 30°, the orientation of the depressions 14 insures that, regardless of the direction from which the incident beam arrives, the angle of incidence with respect to a side wall 18 will always lie within the range which results in a satisfactory return signal.

Figure 5:
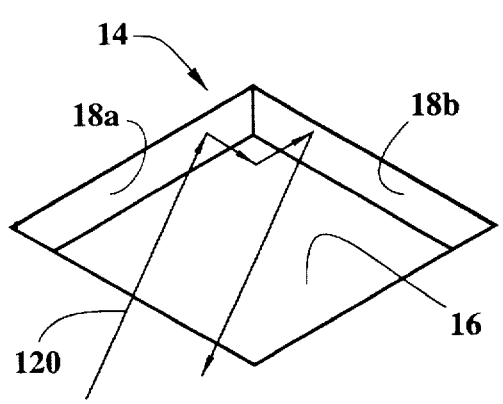
FIG. 5 is a diagram of a depression of the needle of FIG. 1 illustrating the three-dimensional reflection of an ultrasound beam off the side and bottom walls of the depression.

The foregoing discussion and FIGS. 3A, 3B, and 4 illustrate the reflection of an ultrasound beam in two dimensions for the sake of simplicity and clarity. However, it will be appreciated that an ultrasound beam may actually interact with the bottom wall and two side walls. This three-dimensional interaction is illustrated in FIG. 5, which shows an incident ultrasound beam 120 which reflects off a first side wall 18a, then reflects off the bottom wall 16, then reflects off a second side wall 18b before reflecting back along the incident path. While the three-dimensional geometry can quickly get complex, the same principles hold, that is, the angle of reflection is equal to the angle of incidence, and an incident beam reflecting off of two or more perpendicularly oriented walls will reflect back along the incident path.

Figure 6:
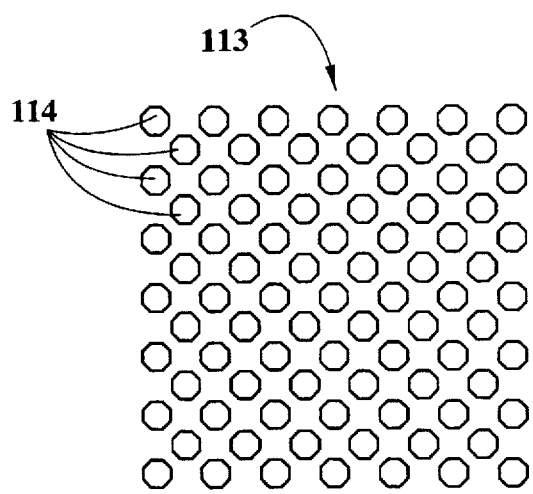
FIG. 6 is a depiction of an alternate pattern of depressions for forming a matrix in the surface of a needle to reflect ultrasound waves in a substantially specular manner.

Different shapes of depressions 14 and different matrix patterns 13 can also be used to enhance the echogenicity of needle 10. FIG. 6 shows a matrix 213 of octagonal depressions 214. The pattern illustrated in FIG. 6 employs a different approach from those previously described, in that all of the depressions 214 are oriented identically, rather than alternate rows and columns being oriented differently with respect to the intervening rows and columns. Applying an analysis similar to that discussed with respect to FIG. 4 above, it can be seen that an incident ultrasound beam will have an angle of incidence with respect to one of the side walls of an octagonal depression 214 which is less than or equal to 22.5°, thereby yielding a satisfactory return signal. Because a portion of the signal striking the base of an octagonal depression 214 will strike an adjoining diagonal side wall and reflect off in a different direction, a somewhat smaller percentage of the incident beam striking a particular depression 214 will be returned. However, this effect is offset by the fact that every octagonal depression 214 will have a wall which provides an angle of incidence less than or equal to 22.5°, rather than only every other depression as was the case with the matrix 13 illustrated in FIG. 2. Since more depressions 214 will result in a satisfactory return signal, the cumulative effect is approximately the same.

To manufacture a needle 10 having a pattern of regularly shaped depressions 14, a print mask technique is used. In general terms, a mask is imprinted on the surface of the needle, and the masked needle is then subjected to a process which removes metal from the unmasked portions of the needle surface.

Prior to printing a mask on a needle blank, adequate surface cleaning of the needle blank is required for good mask adhesion. A cleaner containing nonionic and anionic surfactants seems to work well and leave a contaminate-free surface. A suitable cleaner is Liqi-Det, available from Oakite Products.

Figure 7A:
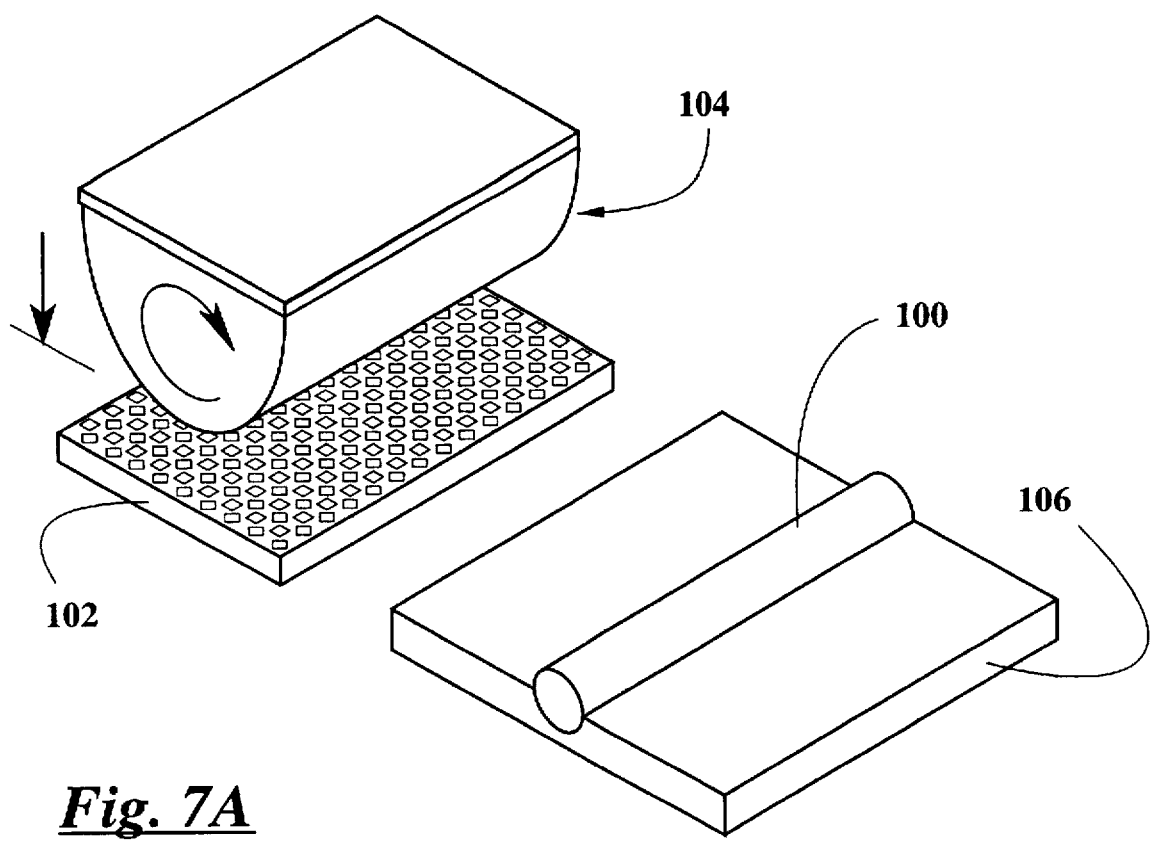
FIG. 7A and 7B illustrate a sequence of steps for imprinting a mask on the surface of a needle.
Figure 7B:
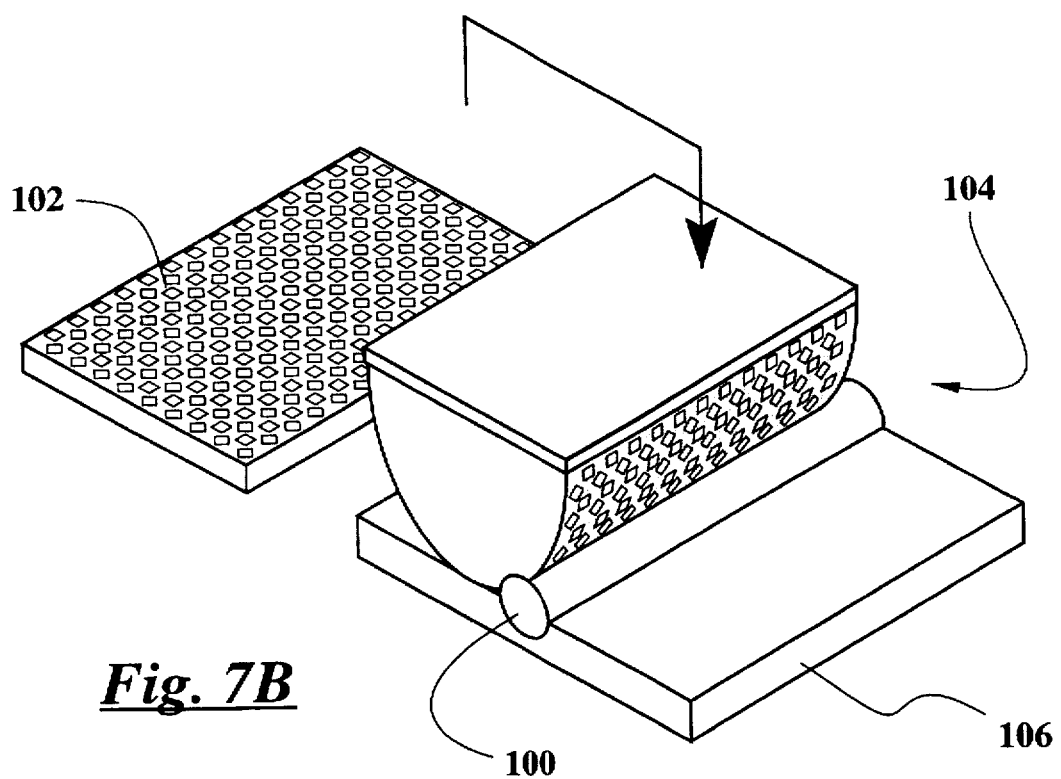

FIGS. 7A and 7B illustrate a method of applying a mask to a rod or needle blank 100. A printing plate 102 is provided which has the pattern of the matrix 13 shown in FIG. 2 on its upper surface. The plate 102 has alternating rows and columns of squares and diamonds etched into its surface. A pad 104 is provided to transfer ink from the plate 102 to the rod 100. A jig 106 is provided with a semicircular recess in its upper surface to hold the rod 100 with the upper half of the rod exposed.

To apply a mask to the rod 100, ink is applied to the plate 102. The pad 104 is then lowered against the plate 102 as shown in FIG. 7A to transfer the pattern of ink to the pad. Then, as illustrated in FIG. 7B, the pad 104 is lifted away from the plate 102, moved over the rod 100, and lowered against the rod. The pattern of ink is transferred from the pad 104 to the surface of the rod 100. The pad 104 is then lifted off the rod 100, the rod rotated 180°, and the process repeated to apply the mask to the other half of the rod.

Figure 8:
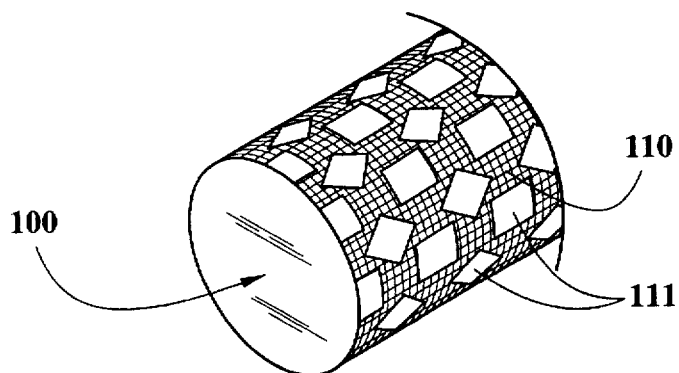
FIG. 8 is a perspective view of a portion of a needle with a mask imprinted on its surface.

FIG. 8 shows the rod 100 with a mask 110 applied to its circumference. Square- and diamond-shaped areas 111 of bare metal are exposed through the mask 110. As will be readily apparent to those skilled in the printing arts, pattern distortion can occur when taking an image off a flat plate 102 and applying the image around a curved surface. In other words, the squares and diamonds printed on the needle blank can take on the shape of a parallelogram. To correct this distortion, the diamonds and squares on the plate 102 must be reshaped somewhat so that after the image has been printed on the needle blank the exposed areas of bare metal desired square or diamond shape. There is no exact science to predicting the amount of distortion, and resultion of this issue requires a trial-and-error approach.

Once the mask has been applied to the needle blank, the ink flash dries in 30 to 60 seconds. The masked rod 100 may then be placed in an oven and heated to chemically cross-link the epoxy in the ink. The cross-linked epoxy exhibits better adhesion to the rod 100. According to a preferred method, the masked needle blank 100 is cured at a temperature of 120° C. for approximately one hour.

Figure 9:
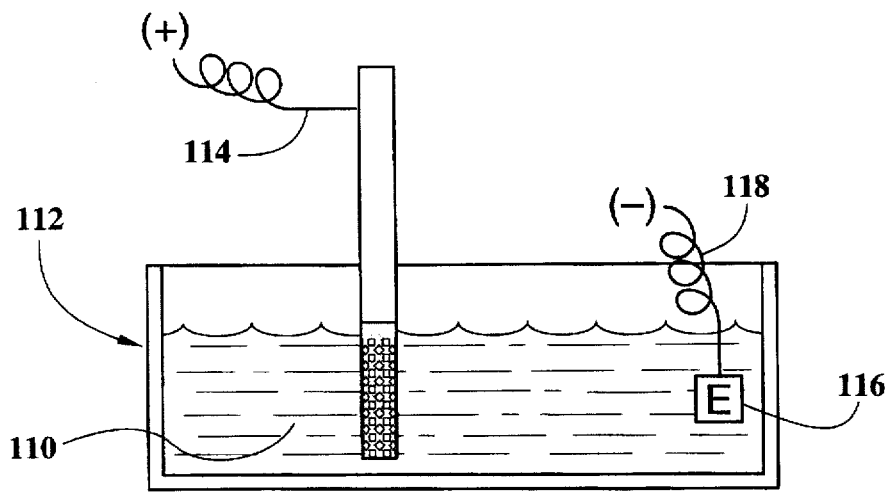
FIG. 9 is a schematic representation illustrating an etching process which forms depressions on the unmasked portions of the surface of the needle of FIG. 8.

Referring now to FIG. 9, the rod 100 with mask 110 is then electro-polished in an electrolyte bath 112. As can be seen in FIG. 9, the needle blank 100 is oriented vertically, and only the masked end of the needle blank is immersed in the electrolyte bath to prevent having to mask the entire length of the needle. A solid band of mask material is applied around the circumference of the rod 100 to a point above the surface of the electrolyte bath 112 to prevent the process from etching an undercut on the needle at the surface of the electrolyte bath.

The electrolyte can be either acid based or a water-based metallic salt solution. An acid-based electrolyte bath provides higher detail and sharper edges to the etched surfaces, while a water-based metallic salt solution avoids problems of acid attacking the ink. A suitable acid-based electrolyte is Power Kleen 500 from Molectrics. A suitable water-based electrolyte is LNC-2 from Lectroetch.

The type of electrolytic solution used in the electro-polishing process will determine the type of ink which is used to mask the rod 100. Regardless of the type of electrolyte used, the ink forming the mask 110 must be non-conductive. However, if an acid-based electrolyte bath is to be used, the ink must also be acid-resistant. A suitable ink for use with either a water-based electrolyte bath or an acid-based electrolyte bath is is TPC 230 from Tekaprint. Another suitable ink for use with a water-based electrolyte bath is TPC 180, also available from Tekaprint. While any color will yield satisfactory results, black is preferable, for reasons which will be explained below.

As shown in FIG. 9, a conductor 114 has one end attached to the rod 100 and the other end attached to the positive pole of an electrical supply. An electrode 116 is placed in the electrolyte bath 112 in spaced apart relation to the rod 100, and a conductor 118 connects the electrode 116 to a negative pole of an electrical supply. Current is then applied. The electro-polishing process etches away at the portions of the rod 100 which are exposed through the mask 110, while the portions of the surface of the rod which are protected by the mask 110 remain unaffected.

Etch depth is precisely controllable by varying the etch time and current. Etch depth is a function of current density. In turn, current density is dependent upon the amount of exposed metal and the current applied. In one example involving an acid-based electrolyte, a current of 100–200 amps at 28 volts is applied for one and a half to two and a half minutes. In an example involving a water-based electrolyte bath, one to four amps, preferably about two amps, of current at 24 volts is applied for one to one and a half minutes.

At the end of the electro polishing process, the rod 100 is removed from the electrolyte bath 112. If an acid-based electrolyte bath was used, the rod 100 will now be dipped in an acid-neutralizing bath. If a water-based metallic salt solution was used as the electrolyte bath, the rod 100 is simply washed off with water.

The next step is to remove the mask 110 from the rod 100. Removal of the ink can be accomplished by a suitable solvent, such as acetone or methyl ethyl keytone. The removal of the ink can be expedited by using a brush with nylon or brass bristles. If the mask 110 was heated to cross-link the epoxy, it may be necessary to heat the rod 100 to break the cross-links in the epoxy before applying the solvent. According to the disclosed method, the rod 100 is heated to a temperature of 700° F. by rolling it over a radiant heater. As previously indicated, black ink is preferred for the mask 110, because black ink absorbs radiant heat more readily. In contrast, the shiny metal of the rod 100 will tend to reflect radiant heat. Thus the mask 110 can be heated to a temperature sufficient to break the cross-links in the epoxy without the temperature of the rod having to be raised to that level.

Once the mask 110 has been removed from the needle blank 100, a finish process is performed on the needle blank. Depending upon the intended use of the needle, angles may be ground on the rod 100 to create one or more cutting surfaces, such as the sharpened cutting surface 12 of the needle 10 shown in FIG. 1. The rod 100, by now formed into a needle 10, is then cleaned to remove surface contaminants, and the needle is insert-molded into a hub. The needle 10 is then sterilized, such as by application of ethylene oxide or by gamma irradiation.

In the disclosed embodiment, the depressions 14 have a depth of 0.0015 inches to 0.003 inches deep, with a width of from about 0.005 to 0.01 inches. Assuming for the sake of example a depression 14 having a width of 0.01 inches, for a 14 gauge needle 10, which has a nominal circumference of about 0.217 inches, approximately eight to ten depressions 14 can be formed in a band around the circumference of the needle.

It is also desirable to select the dimensions of the depressions 14 such that the width of the depression is greater than or equal to the wavelength $\lambda$ of the ultrasound beam. In medical applications, 5 MHz is generally the lowest frequency which will be encountered, with higher frequencies being preferable. A 5 MHz frequency corresponds to a wave length $\lambda$ of approximately 0.0115 inches. Thus for optimum visibility in conjunction with a 5 MHz ultrasound transducer, the depressions 14 should have a width of at least approximately 0.012 inches.

While the foregoing embodiment has been described with respect to the stylet of a core biopsy needle, it will be appreciated that the print mask technique of the present invention is suitable for use on many other types of medical devices which must be visualized under ultrasound. In addition to the stylet of a core biopsy needle, the canula can also be echogenically enhanced using this process. Aspiration biopsy needles and amniocenteses needles are other examples of some medical devices to which the print task technique is applicable. However, where a hollow needle, such as the cannula of a core biopsy needle, is to be echogenically enhanced using this process, it is preferable to prevent the electro-polishing process from attacking the interior surface of the hollow needle. The corrosive effects of the electro-polishing process on the interior surface of the hollow needle can result in failure to meet tolerances for the inner diameter of the needle. In the case of particularly thin-walled hollow needles, the electro-polishing process can attack the interior surface to the extent that the wall of the needle becomes too thin, and the structural integrity of the needle may be compromised. To prevent the electro-polishing process from attacking the interior walls of a hollow needle, either the needle should be plugged to prevent the electrolyte from entering the lumen of the needle, or a flow of air can be directed through the lumen of the needle to prevent the electrolyte from entering.

Finally, it will be understood that the preferred embodiment has been disclosed by way of example, and that other modifications may occur to those skilled in the art without departing from the scope and spirit of the appended claims.

What is claimed is:

1. A method for manufacturing an echogenically enhanced medical device, comprising the steps of:

imprinting a mask on the surface of an object, said mask leaving portions of said surface of said object exposed through said mask; and subjecting said object with said mask imprinted thereon to a process which removes material from said portions of said surface of said object exposed through said mask.

2. The method of claim 1, wherein said object is comprised of metal, wherein said mask is comprised of a non-conductive material, and wherein said step of subjecting said object to a process which removes material from said portions of said surface of said object exposed through said mask comprises electro-polishing said object.

3. The method of claim 2, wherein said process of electro-polishing said object comprises the steps of:

immersing said object in an electrolyte bath;

immersing an electrode in said electrolyte bath in spaced-apart relation to said immersed object;

passing an electric current from said object to said electrode, whereby material is removed from said portions of said surface of said object exposed through said mask.

4. The method of claim 3, wherein said electrolyte bath is comprised of a water-based metallic salt solution.

5. The method of claim 3, wherein said electrolyte bath is comprised of an acid-based solution.

6. The method of claim 5, wherein said non-conductive material comprising said mask is an acid-resistant material.

7. The method of claim 1, wherein said step of imprinting a mask on the surface of an object comprises the step of imprinting a mask on the surface of an object with an epoxy material, and comprising the further step of:

prior to said step of subjecting said object with said mask imprinted thereon to a process which removes material from said portions of said surface of said object exposed through said mask, heating said mask to a temperature sufficient to cross-link said epoxy material to improve bonding of said mask to said object.

8. The method of claim 1, wherein said step of imprinting a mask on the surface of an object and leaving portions of said surface of said object exposed through said mask comprises the step of imprinting a mask having a plurality of rectangular openings therein.

9. The method of claim 8, wherein said plurality of rectangular openings comprises rows of rectangular openings, and wherein rectangular openings in alternate rows are aligned with the sides of said rectangular openings oriented at a 45° angle with respect to the sides of said rectangular openings in the remaining rows.

10. An echogenically enhanced medical device, comprising:

a body comprised of an echogenically reflective material;

a plurality of depressions formed in the surface of said body, said depressions having substantially straight sides and substantially flat bottom and side walls.

11. The device of claim 10, wherein said plurality of depressions comprises a plurality of square depressions.

12. The device of claim 11, wherein said plurality of square depressions comprises rows and bands of square depressions having two sides substantially parallel to an axis, interspaced by alternate rows and bands of square depressions having two sides oriented substantially diagonally with respect to said axis.

13. The device of claim 11, wherein each of said plurality of depressions has a depth which is approximately 20% to 40% of the length of a side of one of said plurality of square depressions.

14. The device of claim 11, wherein each of said plurality of depressions has a depth of from about 0.0015 inches to about 0.003 inches, and wherein each of said plurality of depressions has a width of from about 0.005 to 0.01 inches.

* * * * *